United States Patent [19]
Kimber et al.

[11] Patent Number: 6,068,614
[45] Date of Patent: May 30, 2000

[54] PLASTIC SYRINGE WITH OVERCAP

[75] Inventors: Michael Browning Kimber, Berowra Waters; Frank Alexander Popovsky, Tahmoor, both of Australia

[73] Assignee: Astra Pharmaceuticals PTY, Ltd., New South Wales, Australia

[21] Appl. No.: 08/836,079

[22] PCT Filed: Oct. 31, 1995

[86] PCT No.: PCT/AU95/00723

§ 371 Date: Jun. 23, 1997

§ 102(e) Date: Jun. 23, 1997

[87] PCT Pub. No.: WO96/14100

PCT Pub. Date: May 17, 1996

[30] Foreign Application Priority Data

Nov. 3, 1994 [AU] Australia ............................. PM9223

[51] Int. Cl.⁷ ................................................. A61M 5/24
[52] U.S. Cl. .................. 604/200; 604/192; 604/238; 604/244; 604/256; 604/263; 264/478
[58] Field of Search ...................... 604/110, 181, 604/187, 192, 199, 200, 236, 238, 244, 256, 263, 111; 215/DIG. 3, 211, 249, 250, 251, 253, 354, 316, 320, 325; 264/464, 478, 176.1, 211.12, 209.1

[56] References Cited

U.S. PATENT DOCUMENTS

| 2,677,374 | 5/1954 | Burnside et al. | 604/199 |
| 4,043,334 | 8/1977 | Brown et al. | 604/199 |
| 4,084,588 | 4/1978 | Koenig | 604/242 |
| 4,253,459 | 3/1981 | Willis | 604/263 |
| 4,390,016 | 6/1983 | Riess | 604/194 |
| 5,135,496 | 8/1992 | Vetter et al. | 604/199 |
| 5,531,707 | 7/1996 | Kers et al. | 604/199 |
| 5,624,405 | 4/1997 | Futagawa et al. | 604/263 |

*Primary Examiner*—Ronald K. Stright, Jr.
*Attorney, Agent, or Firm*—Vidas, Arrett & Steinkraus, P.A.

[57] ABSTRACT

A plastic pre-filled syringe which includes an open ended barrel sealed at one end by a moveable stopper and sealed at the other end by a closure frangibly connected to the syringe. The syringe also includes an overcap which can be moved so to engage with the closure whereby removal of the overcap will cause the closure to be separated from the rest of the syringe and reveal the contents for injection.

17 Claims, 3 Drawing Sheets

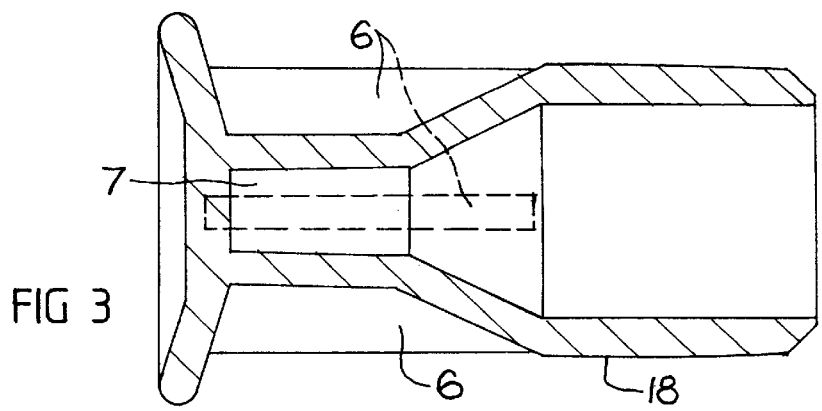
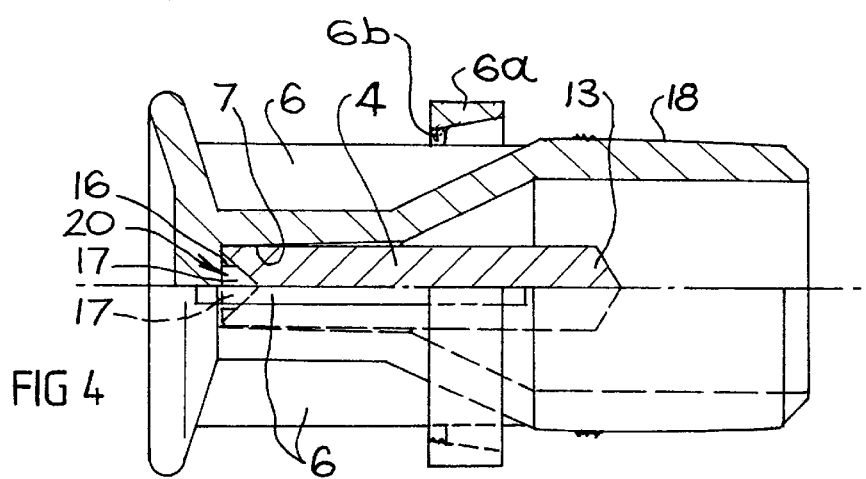
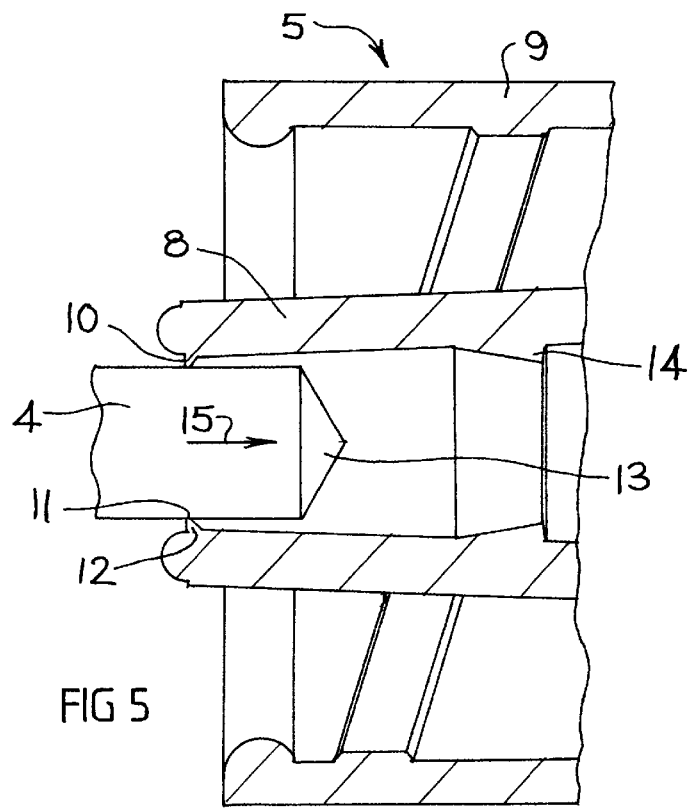

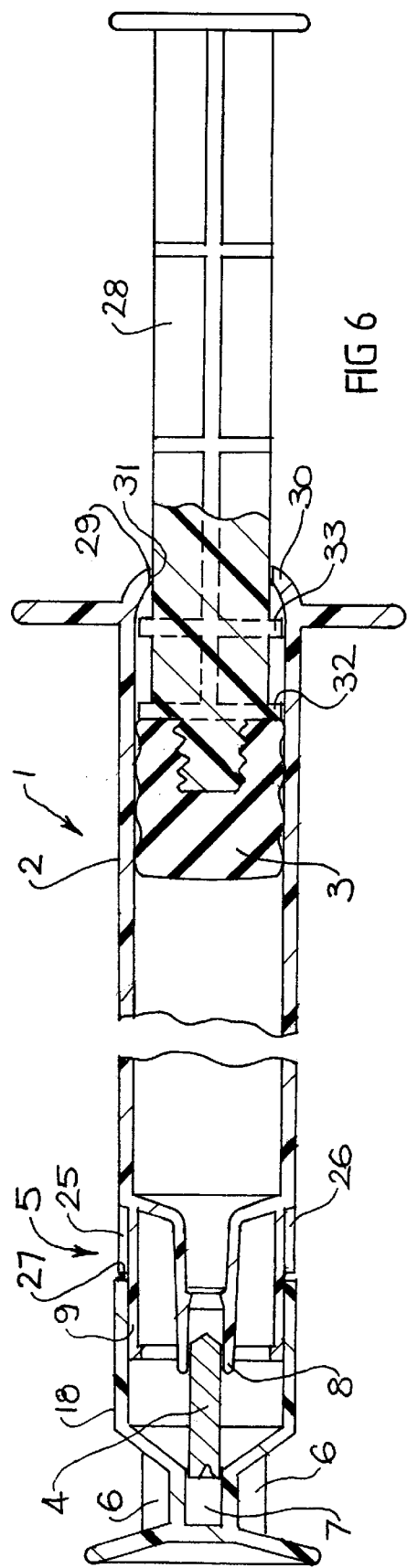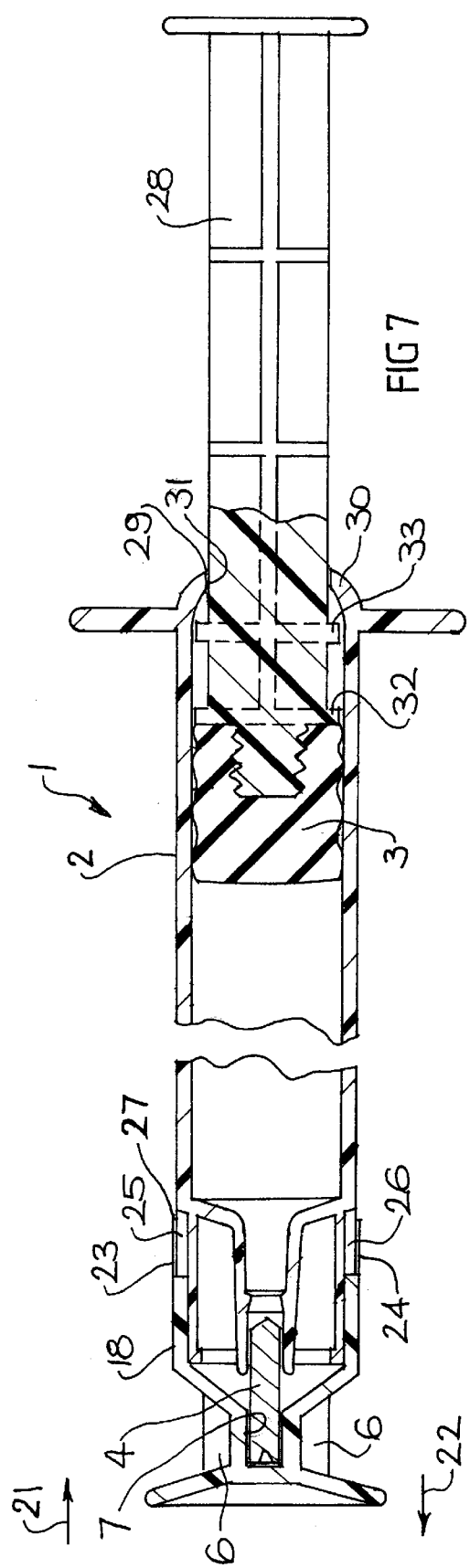

PLASTIC SYRINGE WITH OVERCAP

BACKGROUND OF THE INVENTION

1. Field of the Invention

This invention relates to a syringe and in particular to a plastic syringe suitable for use as a pre-filled product.

2. Description of the Related Art

In recent years, there have been significant shifts in medical practice due to an increasing awareness of the risks of transfer of various transmissible viruses such as AIDS—HIV and hepatitis especially when treating a number of patients. In particular, medical practitioners are increasingly alert to the risks of virus transfer associated with the re-use of surgical and other medical apparatus. For this and other reasons, there are stronger calls for reliable and easy to use medical and surgical appliances which are disposable after a single use. This is particularly so when it comes to hypodermic syringes. As hypodermic needles come into contact with bodily fluids there is a risk of cross infection if the same syringe is used more than once—even if the actual hypodermic is disposed of after each use. Pre-filled disposable syringes are in demand for these and other reasons. A single dose product already accurately filled and labelled with the name of the injectable is convenient and moreover safer to use as there is lower risk of incorrect dosing on administration. It is used once and discarded. There is no need to re-sterilize the equipment and there is no need to carefully transfer the injectable from a separate ampoule.

An example of a pre-filled syringe is described in the Applicant's Australian patent 595096. The syringe described in that patent is sealed at one end by al stopper and at the other by a closure which is integral with the syringe. The closure is adapted to be removed so that after removal a hypodermic needle may be fitted to the end of the syringe for injection of the contents. The closure is described as being removable by twisting with an appropriate shaped tool or by snap action.

A further example of a pre-filled syringe is described in the Applicant's Australian patent 635631 wherein the syringe described is also fitted with an integral closure. The closure is adapted to be broken from the end of the syringe on the application of a hypodermic needle onto the needle fitting on the syringe. The closure is moved into the syringe and retained within a chamber at the needle end of the syringe.

Whilst both of the aforementioned products represented significant improvements over other prior pre-filled syringes, the present invention relates to a variation in syringe design which brings with it certain advantages (in some applications) over both of the previously described products which will be apparent from the following more detailed discussion.

SUMMARY OF THE INVENTION

The present invention involves the use of a protective overcap which can be used to remove an integral closure on a pre-filled syringe. The invention has particular application in conjunction with a syringe of the type described and defined in Australian patent 635631 but is not limited to such a syringe. It is especially suited to applications where the pre-filled syringe is intended to be used without a hypodermic needle such as when introducing a pharmaceutical solution from a syringe into an intravenous drip.

Thus, according to the present invention there is provided a plastic pre-filled syringe which includes:

(a) an open ended barrel sealed at one end by a moveable stopper and sealed at the other end by a closure frangibly connected to the syringe; and (b) an overcap shaped to fit over at least the end of the closure;

said overcap including closure retention means adapted to hold and retain at least the end of the closure such that upon removal of the overcap from the rest of the syringe the closure will be separated so to reveal the contents for injection.

DESCRIPTION OF PREFERRED EMBODIMENTS

Preferably, the overcap is adapted to move from a position in which it is fitted over the end of the closure but in which the closure is not retained within the closure retention means to a position where it is fitted over the end of the closure and the closure is firmly retained within the closure retention means.

Preferably, the closure is in the form of a stem which extends outwardly from the end of the syringe remote from the stopper and the closure retention means is a hollow channel within the overcap into which the stem can be inserted. The closure can be held and retained in the closure retention means in this embodiment in a number of ways as will be apparent to those skilled in the art. For example, either the stem or the aperture may include ribbing or the like to cooperate with a groove in the other so that the stem when pushed far enough into the channel will "lock" into the overcap. An appropriate removal force applied to the overcap will result in rupture of the seal of the closure to the syringe so that the overcap and closure will be removed in a single action. Most preferably, the hollow channel includes a portion which is slightly tapered internally so that it progressively narrows in diameter.

In such an embodiment the application of a downwards force onto the overcap can be used to move the overcap down and force the end of the closure tightly into the channel prior to the application of a removal force to remove the overcap (and closure) from the end of the syringe. Where the closure retention means is a hollow channel and the closure is an outwardly extending stem it is preferred that the stem be between 1.5 mm and 2.3 mm in maximum cross-section. More preferably, it is between 1.8 mm to 2.1 mm in maximum cross-section. The channel preferably includes a retention section which is at least 0.1 mm smaller in maximum cross-section. In this embodiment, it is preferred that the entrance of the channel be at least 0.1 mm wider than the stem and that the channel include a longitudinally tapered section that tapers at between 1 to 3° (most preferably at about 1.5°). Alternatively, the channel can be of substantially uniform cross-sectional diameter and the stem can be tapered.

In these arrangements, the end of the closure may comprise a plurality if longitudinal grooves or flutes and be formed from a compressible but resilient plastics material. In this form, the closure thus includes a plurality of fins which are more readily compressed when forced into the channel in the overcap. This enhances the retention of the closure in the channel for removal from the end of the syringe.

In one embodiment of the invention the closure end of the syringe includes a simple exit orifice through which the contents of the syringe may be expressed once the closure has been removed. In an alternate embodiment, the closure end of the syringe includes a fitting suitable for accommodating a hypodermic needle supported on a plastic holder.

For example, the fitting at the end of the syringe may be in the form of a hollow conical section surrounded by but spaced from a peripheral outer wall. The inside surface of the outer wall may include a screw thread such as in a standard "luer lock" needle fitting. In this embodiment, the closure is sealingly connected to the conical section of the needle fitting aid projects beyond the end of the fitting. Preferably, the closure also extends inwardly into the hollow conical section and is frangibly connected to the inside wall of the conical section at a location distanced from the inner end of the closure.

The connection of the closure to the end of the syringe should preferably be strong enough to withstand accidental knocking or dropping of the syringe if the overcap has been removed but frangible enough to rupture on the application of a removal force created by withdrawal of the overcap once the remote end of the closure has been retained in the closure retention means in the overcap. In the preferred embodiment where the closure is squeezed within a channel in the overcap, the frictional force of the stem in the channel should be greater than that required to rupture the frangible connection between the closure and the end of the syringe.

Preferably, the connection of the closure to the end of the syringe is provided by a bridging portion of plastics material which extends from the inner wall of an exit orifice at the end of the syringe to the outer wall of the closure. Most preferably, the bridging portion comprises a section of minimum cross-section and another section which uniformly increases in thickness away from the section of minimum cross-section. Desirably, the section of minimum cross-section is that section of the bridging portion closest to the outer wall of the closure.

The overcap should be of such size and shape that it covers and protects the closure from accidental abuse. It is desirable that the overcap include a gripping portion at its end to facilitate removal, e.g. a finger gnp or outwardly extending flange. Preferably, the overcap is secured into position over the closure. This may be readily achieved by spot welding the overcap to the end of the syringe. In the embodiment of the invention where the end of the syringe includes a "luer-lock" or similar type of needle fitting the overcap preferably has a depending peripheral skirt which is of such diameter and thickness to fit between the hollow conical section and the peripheral outer wall of the needle fitting. Alternatively, in cases where it is considered desirable to protect the outer surface of the peripheral outer wall from contamination the overcap may include al depending peripheral skirt which is of such diameter to fit over the outer surface of the peripheral outer wall. As will be apparent to those skilled in the art, if greater precision of operation is required the overcap may incorporate two depending peripheral skirt portions spaced apart by a distance slightly greater than the thickness of the peripheral outer wall and positioned so to fit on either side of the peripheral outer wall. The overcap is preferably secured in position by spot welding the outer surface of the skirt to the inner surface of the peripheral outer wall.

Preferably the overcap is secured into position over the closure and with the end of the closure in the entrance but not engaged within the closure retention means. In one embodiment of the invention, the overcap has a depending peripheral skirt positioned to fit between the conical section and the peripheral outer wall of a luer lock fitting and incorporates an outer ring frangibly connected to the upper end of the depending peripheral skirt. The outer ring is positioned to abut against the top of the peripheral outer wall when the overcap is positioned over the closure with the end of the closure in the entrance but not engaged within the closure retention means. In this way, the syringe may be opened in an easy two step action wherein the overcap is first pushed in (to break the frangible ring from the overcap and engage the end of the closure in the closure retention means) and pulled out (to remove the overcap and closure and reveal the contents of the syringe for injection).

In an alternative embodiment utilizing a luer lock finish but where the depending peripheral skirt is spot welded to the peripheral outer wall, the syringe may be opened using a three step action wherein the overcap is first twisted (to break the seal with the end of the syringe), pushed in (to engage the end of the closure in the closure retention means) and pulled out (to remove the overcap and closure and reveal the contents of the syringe for injection).

In this embodiment, the syringe body and the overcap may usefully incorporate a co-operating tooth and recess configuration which are offset from one another at the position at which the overcap is welded to the peripheral outer wall. For example, a pair of teeth may be moulded onto opposite sides of the peripheral outer wall and the overcap may incorporate matching recesses which are offset from the respective teeth on the peripheral outer wall when the overcap is welded into position. If the teeth are shaped to abut against the bottom end of the peripheral outer wall when located in this position this interaction can operate to prevent accidental engagement of the closure in the overcap as the overcap could not be pushed in. However, when an operator intends to open the syringe for use the cap can be twisted to break the seal with the end of the syringe and the co-operating teeth and recesses can be thereafter aligned so to enable the operator to push the cap in so to engage the end of the closure in the closure retention means.

It will be appreciated that the syringe described and defined in Australian patent 635631 can be used in conjunction with an overcap having the requisite features as previously discussed to produce a composite product of the invention. In a syringe of that type the user would have two options, i.e. removal of the closure by the overcap or rupture of the closure connection by attachment of an hypodermic syringe once the overcap has been removed (if it has not been used to remove the closure). This gives the user flexibility in use as the same product can be used easily for connection to a part in an intravenous drip (where no hypodermic is attached) or as a hypodermic syringe with simple and effective opening of the syringe in one of two ways.

The syringe of the invention is preferably made from an elastomer such as polypropylene, polyethylene or polyethylene terephthalate. Most preferably, it is injection moulded from polypropylene.

Any of the aforementioned embodiments of the invention may be partially or completely manufactured in an aseptic environment to ensure the sterility of the contents of the syringe.

Preferably, the syringe barrel and the overcap are both separately injection moulded in an aseptic environment. The syringe is then filled with a pre-sterilized injectable. Once filled, a stopper is delivered to the aseptic environment in a pre-sterilized condition and inserted into the open end of the syringe barrel.

The cap is inserted over the end of the closure and is preferably welded (e.g. by ultrasonic welding) to the closure end of the barrel. All of these steps are preferably conducted in the aseptic environment. In a preferred process, the syringe thereafter exits the sterile area is and then off loaded for terminal sterilization. The syringe is then preferably delivered to a plunger rod and insertion machine. At this stage, if desired, the completed pre-filled syringe may be removed and taken to a terminal sterilizer. The process may be further extended such that the plunger rod insertion, labelling and inspection are also done in the sterile area.

Thus, in accordance with another aspect of the current invention there is provided a method of manufacturing a plastic pre-filled syringe which includes:

i) injection moulding an open ended barrel sealed at one end by an integral closure frangibly connected to the barrel in an aseptic environment;

ii) aseptically filling the barrel with an injectable medium in said aseptic environment;

iii) introducing into the aseptic environment a pre-sterilized stopper;

iv) fitting the pre-sterilized stopper into the open end of the barrel in the aseptic environment;

and either before, during or after the filling of the barrel separately injection moulding an overcap which includes closure retention means and fitting said overcap over the closure, and connecting it to the closure end of the barrel.

The overcap connection and moulding do not need to be conducted within the aseptic environment but preferably they are.

BRIEF DESCRIPTION OF THE DRAWINGS

A preferred embodiment of the invention is hereafter described with reference to the following drawings in which:

FIG. 3 is an enlarged cross-sectional view of the overcap;

FIG. 4 is a cross-sectional view of the overcap shown in FIG. 3 once removed from the rest of the syringe retaining the closure within it;

FIG. 5 is an enlarged sectional view of the needle fitting end of the syringe showing the closure connection prior to removal.

FIG. 6 is a cross-sectional view of a further embodiment of the invention illustrating a syringe which has moulded teeth shaped and located to co-operate with recesses formed in the overcap. This figure shows the overcap in position prior to engagement and retention of the closure in the overcap; and FIG. 7 is a cross-sectional view of the syringe shown in FIG. 6 with the overcap rotated and pressed in so that the teeth on the syringe body and the recesses on the overcap are engaged and the closure retained in the overcap.

In FIG. 1, there is illustrated a syringe 1 which comprises an open ended barrel 2. The barrel 2 is sealed at one end by a moveable stopper 3 and is sealed at the other end by a closure 4. The closure 4 is in the nature of a stem which is connected to the needle fitting end 5 of the syringe 1. An overcap 6 is positioned over the top of the closure 4 and is attached to the needle fitting end 5 of the syringe. The overcap 6 includes a frangibly connected ring 6a which inhibits downward movement of the overcap 6. Ring 6a is connected to the outer wall of overcap 6 by frangible bridges 6b and abuts against the end of the needle fitting end 5 of the syringe. The overcap 6 also includes a hollow channel 7.

Figure 1:
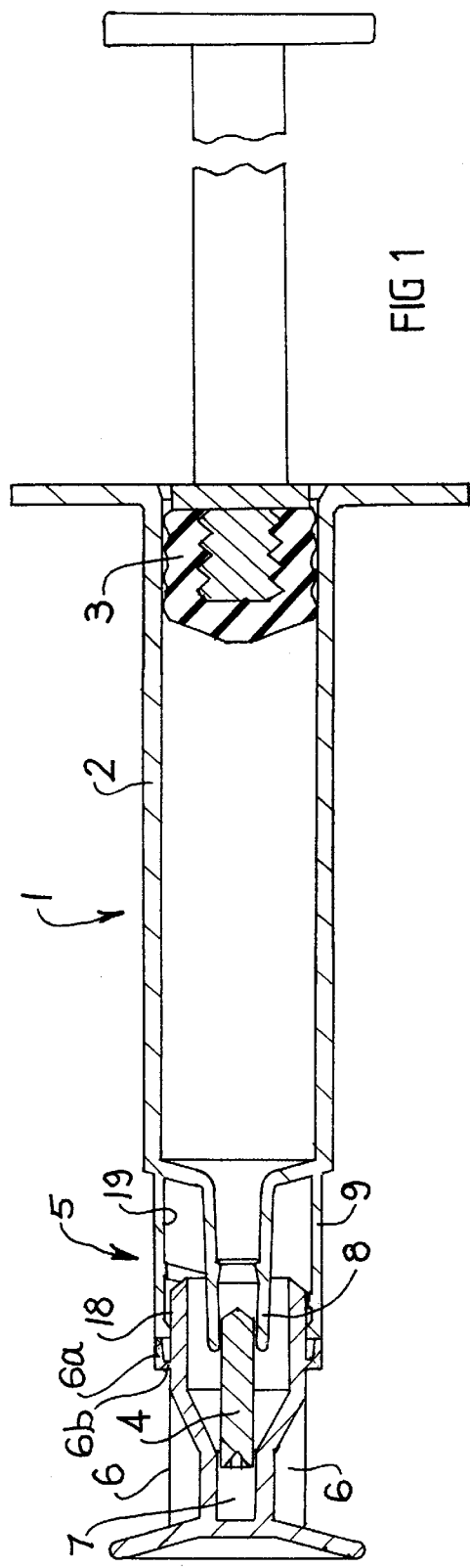
FIG. 1 is a cross-sectional view of a syringe of the invention with the overcap connected to the end of the syringe prior to engagement with the closure.

The overcap end 6 is connected to the end of the syringe by spot welding.

The needle fitting end 5 is in the nature of a luer-lock fitting and is shown in greater detail in FIG. 5. In particular, needle fitting end 5 includes a hollow conical portion 8 surrounded by a peripheral wall 9. The closure 4 is attached to the conical portion 8 by a frangible bridging portion 10. Bridging portion 10 comprises a portion of minimum cross-section 11 and a section 12 of broadening thickness which is attached to the inner wall of conical portion 8. The applicant has found that if the bridging portion is configured in this way it enhances a clean and consistent break when the closure 4 is removed. Preferably, the closure 4 includes end portion 13 which is conical in profile. The internal wall of the conical portion 8 also includes stop 14 dimensioned so to prevent the closure 4 from falling within the body of the syringe should the syringe be opened by pushing the closure downwards in the direction of arrow 15.

Turning to FIG. 4, it will be seen that closure 4 comprises grooves 16 separated by fins 17.

FIG. 1 shows overcap 6 positioned over closure 4 and connected to the needle fitting end 5 by spot welding outer wall 18 of the overcap 6 to the inside surface 19 of peripheral wall 9. The end of closure 4 is positioned adjacent to the opening of channel 7.

In use, overcap 6 is rotated so to break its connection with the end of needle fitting end 5. It is then pushed in the direction of arrow 21 so that ring 6a is, separated from overcap 6 and so that closure 4 is pushed into and retained within channel 7. The closure 4 is held tightly within the closure as channel 7 is of gradually reducing diameter; tapering inwardly at an angle of about 1.5 degrees from opening 20.

Once closure 4 has been retained with overcap 6, the overcap is pulled outwardly in the direction of arrow 22 bringing the closure with it as shown in FIG. 4. The closure breaks away from conical portion 8 of needle fitting end 5 by rupture of the minimum cross-sectional portion of bridging portion 10. Removal of the closure effectively opens the syringe so that the injectable contained within the barrel is available for injection. A hypodermic needle (not shown) may be fitted to the needle fitting end 5 or alternatively the syringe may be attached to an appropriate port for introducing the injectable into a drip or in similar such application.

Figure 2:
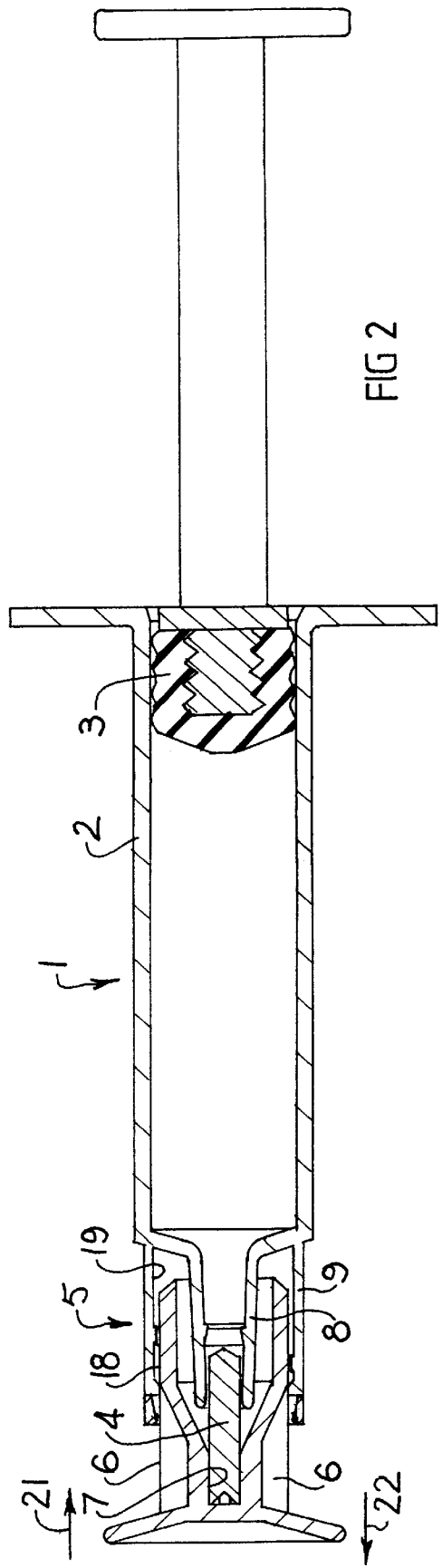
FIG. 2 is a cross-sectional view of the syringe shown in FIG. 1 with the overcap pressed in and the closure retained within the overcap.

In FIG. 6, an alternative embodiment of the invention is shown. The needle fitting end 5 of the syringe is similar to that as shown in FIG. 1. Like features are shown by reference to the same numerals as used in the description of the embodiments shown in FIGS. 1 and 2. In this syringe, the overcap is wider and outer wall 18 is disposed so to be located on the outer side of peripheral wall 9. Outer wall 18 of overcap 6 incorporates recesses 23 and 24 which can be seen in FIG. 7. Needle fitting end 5 incorporates teeth 25, 26 which are of the requisite length to abut or be closely adjacent to the end wall 27 of outer wall 18 when the overcap 6 is positioned with closure 4 adjacent to the entrance of channel 7. In the configuration shown in FIG. 6, recesses 23 and 24 are offset from the teeth 25, 26. In the embodiment shown in FIG. 6, it is intended that overcap 6 is spot welded so to be connected to syringe 1 in the orientation as shown in FIG. 6. In use, an operator twists overcap 6 so to break the spot welding so that overcap 6 can thereafter be moved. The overcap 6 is rotated to a position where recesses 23, 24 are in alignment with teeth 25, 26. In this position, the overcap 6 is then pushed in the direction of arrow 21 to a position as shown in FIG. 7. In this position, closure 4 is engaged and retained within channel 7. As with the embodiment shown in FIGS. 1 and 2, a removal force in the direction of arrow 22 will result in closure 4 being removed so to reveal the contents of the syringe for injection. In the embodiment shown in FIGS. 6 and 7, the opposite end of syringe 1 is configured so to reduce the prospect of unauthorised tampering and removal of the contents from the syringe. Stopper 3 is attached to a plunger rod 28 and the plunger assembly extends through open end 29. In the illustrated arrangement, the opening is defined by a collar 30 which incorporates a free end 31 which extends inwardly from the inner wall of barrel 2. In this way, the opening 29 is constricted as compared to the chamber bore. The plunger assembly extends through the opening 29. An abutment disc 32 extends outwardly from the plunger rod 28 adjacent to the stopper 3. A further disc 33 is spaced from disc 32. Discs 32, 33 and collar 30 operate in conjunction to inhibit unauthorised withdrawal of the injectable solution from the body of the syringe.

It will be appreciated having regard to the foregoing examples of preferred embodiments that the present invention provides significant flexibility for the user. The closure may be removed via the retention means in the overcap or by placement of a hypodermic needle onto the needle fitting once the overcap has been removed. The syringe may be pre-filled with a marked and known amount of a particular injectable and this provides convenience and ease of use for the practitioner.

It will be appreciated that additions and/or alterations may be made to the preferred embodiments as described hereinbefore without departing from the spirit and ambit of the invention as defined in the following claims.

What is claimed is:

1. A plastic pre-filled syringe which includes:
    (a) an open ended barrel sealed at one end by a moveable stopper and sealed at the other end by a closure frangibly connected to the syringe; and
    (b) an overcap which includes closure retention means able to hold and retain at least the end of the closure; wherein said overcap is moveable from a first position, from which removal of said overcap will not cause the frangible connection of the closure to the syringe to be broken, to a second position in which the closure is held and retained by the closure retention means and from which removal of the overcap will cause the closure to be separated from the rest of the syringe so to reveal the contents for injection.

2. A plastic syringe as claimed in claim 1 wherein the closure is in the form of a stem which extends outwardly from the end of the syringe remote from the stopper.

3. A plastic syringe as claimed in claim 2 wherein the closure retention means is a hollow channel within the overcap into which the stem can be inserted.

4. A plastic syringe as claimed in claim 3 wherein the hollow channel includes a portion which is tapered internally so that it progressively narrows in diameter.

5. A plastic syringe as claimed in claim 4 wherein the stem is between 1.5 mm to 2.3 mm in maximum cross-section and the channel in the overcap includes a section which is at least 0.1 mm smaller in maximum cross section than the stem.

6. A plastic syringe as claimed in claim 5 wherein the stem is between 1.8 mm to 2.1 mm in maximum cross-section.

7. A plastic syringe as claimed in claim 1 wherein the closure end of the syringe includes a fitting suitable for accommodating a hypodermic needle.

8. A plastic syringe as claimed in claim 7 wherein the fitting is a luer-lock needle fitting which includes a hollow conical section and a peripheral outer wall.

9. A plastic syringe as claimed in claim 8 wherein the overcap includes a depending peripheral skirt which is of such diameter and thickness to fit between the hollow conical section and the peripheral outer wall of the needle fitting.

10. A plastic syringe as claimed in claim 8 wherein the overcap includes a depending peripheral skirt which is of such diameter to fit over the outside of the peripheral outer all of the needle fitting.

11. A plastic syringe as claimed in claim 1 wherein the closure is frangibly connected to the end of the syringe by a bridging portion of plastics material which extends from the inner wall of an exit orifice at the end of the syringe to the outer wall of the closure.

12. A plastic syringe as claimed in claim 11 wherein the bridging portion comprises a section of minimum cross-section and another section which increases in thickness away from the section of minimum cross section.

13. A plastic syringe as claimed in claim 1 wherein the closure comprises a plurality of longitudinal grooves each separated by a compressible fin.

14. A plastic syringe as claimed in claim 1 wherein the overcap is secured into position over the closure.

15. A plastic syringe as claimed in claim 1 wherein said syringe is made exclusively from polypropylene, polyethylene or polyethylene terephthalate.

16. A method of manufacturing a plastic pre-filled syringe which includes:
    i) injection moulding in an aseptic environment an open ended barrel sealed at one end by an integral closure frangibly connected to the barrel;
    ii) aseptically filling the barrel with an injectable medium in said aseptic environment;
    iii) introducing into the aseptic environment a pre-sterilized stopper;
    iv) fitting the pre-sterilized stopper into the open end of the barrel in the aseptic environment;
    and either before, during or after the filling of the barrel separately injection moulding an overcap which includes closure retention means and fitting said overcap over the closure, and connecting it to the closure end of the barrel.

17. A method as claimed in claim 16 wherein said overcap is moulded within the same aseptic environment as that in which the open ended barrel is injection moulded and the overcap is connected to the closure end of the barrel within said aseptic environment.

* * * * *